United States Patent [19]

Fleck

[11] Patent Number: 4,834,710
[45] Date of Patent: May 30, 1989

[54] CATHETER SHIELD AND TEST STRUCTURE

[75] Inventor: Philip B. Fleck, Douglassville, Pa.

[73] Assignee: Arrow International Investment Corporation, Wilmington, Del.

[21] Appl. No.: 107,400

[22] Filed: Oct. 8, 1987

[51] Int. Cl.$^4$ .................... A61M 5/00; A61M 25/00
[52] U.S. Cl. ................................... 604/171; 604/163
[58] Field of Search ................... 604/171, 172, 163; 206/365, 438

[56] References Cited

U.S. PATENT DOCUMENTS

| | | | |
|---|---|---|---|
| 3,544,668 | 7/1968 | Dereniuk | 604/103 X |
| 3,648,704 | 3/1972 | Jackson | 604/172 |
| 3,683,928 | 8/1972 | Kuntz | 604/171 |
| 3,991,762 | 11/1976 | Radford | 604/172 |
| 4,327,723 | 5/1982 | Frankhouser | 604/171 X |
| 4,392,853 | 7/1983 | Muto | 604/171 |
| 4,515,592 | 5/1985 | Frankhouser | 604/171 |
| 4,568,334 | 2/1986 | Lynn | 604/172 |
| 4,622,033 | 11/1986 | Taniguchi | 604/172 |
| 4,637,404 | 1/1987 | Gessman | 128/786 |
| 4,696,296 | 9/1987 | Palmer | 128/207.16 |

FOREIGN PATENT DOCUMENTS

WO86/01119 12/1984 Int'l Pat. Institute .

OTHER PUBLICATIONS

E. Kopman, MD and J. Sandza, MD, "Manipulation of the Pulmenary-artery Catheter after Placement: Maintenance of Sterility", *Anesthesiology*, The Amer. Society of Anethesiologists, Inc., May 1978, vol. 48, No. 5, pp. 373-374.

Primary Examiner—Dalton L. Truluck
Attorney, Agent, or Firm—Charles H. Lindrooth

[57] ABSTRACT

Equipment is disclosed for shielding a catheter such as a balloon-tipped vascular catheter from contamination during testing and insertion and for shielding a substantial reserve catheter section for use if catheter re-positioning is necessary. As shown, the structure includes two interconnecting envelopes which physically isolate the catheter. One envelope is designed to shield the distal end portion of the catheter during testing for luman patency and balloon inflation. The other envelope is extendible to cover the entire length of catheter intended for insertion into the patent upon completion of required tests. The second envelope thereafter provides a means for advancement or re-positioning of the catheter or withdrawal of the same without physical contact by the hands or exposure to airborne contaminants.

17 Claims, 2 Drawing Sheets

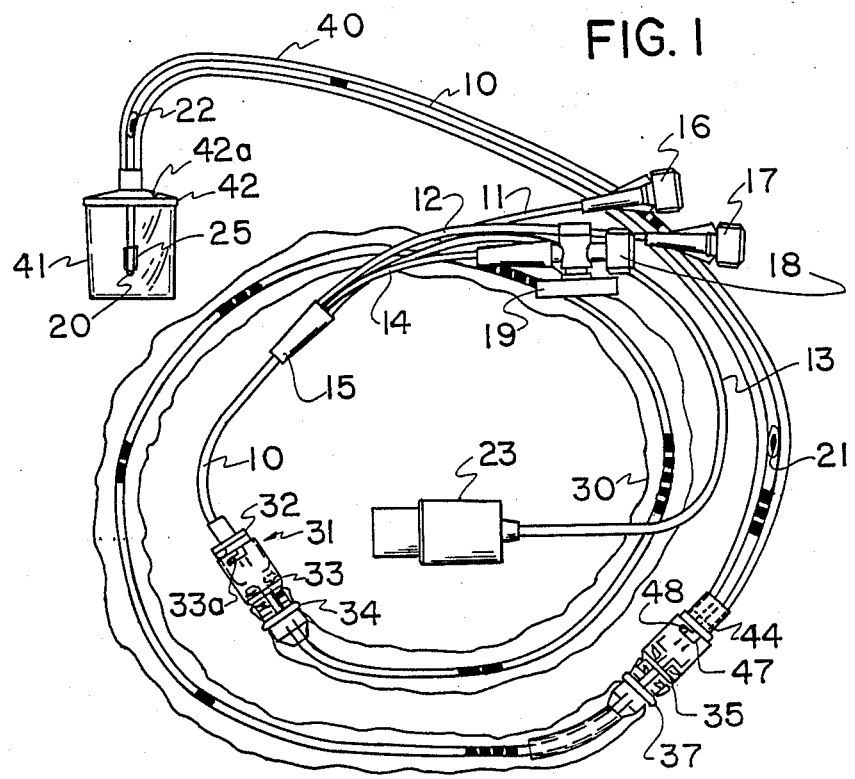
FIG. 1
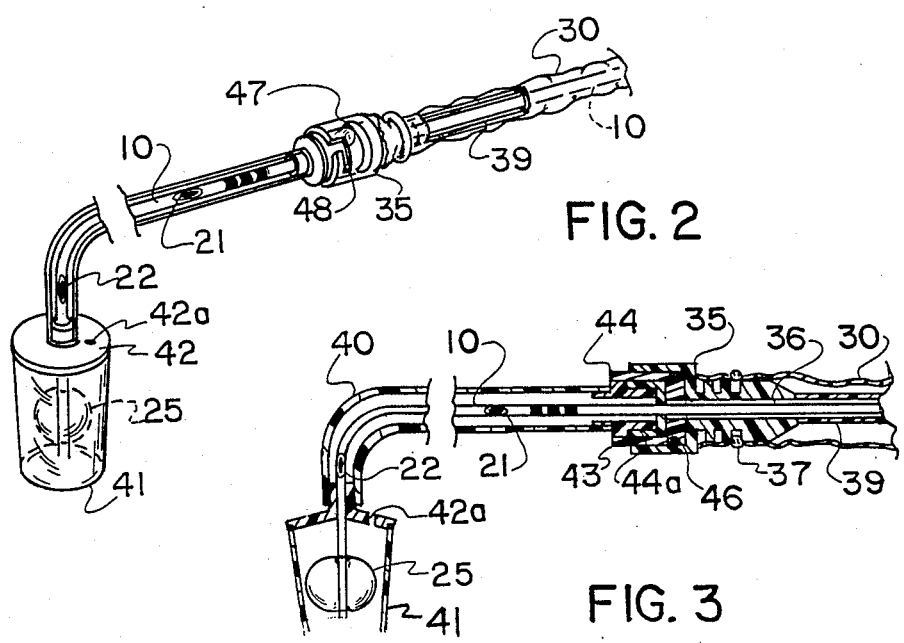
FIG. 2
FIG. 3

CATHETER SHIELD AND TEST STRUCTURE

FIELD OF THE INVENTION

This invention relates to catheters such as intravascular catheters and more particularly to equipment for maintaining the sterility of such catheters by physically isolating all portions of a catheter intended for insertion into a patient's blood vessel or other body cavity from the time the seal or the container in which the catheter is stored is broken, during testing and insertion and during subsequent use.

BACKGROUND OF THE INVENTION AND THE PRIOR ART

The development of apparatus and techniques for maintaining the sterility of catheters, such as thermodilution flow-directed balloon catheters used for measuring cardiac output and for obtaining other diagnostic data, has received critical attention as the use of such products has expanded. The packaging of the catheter in gas-sterilizable containers and in single-use kits having all of the items needed for insertion of the catheter and for use in carrying out the required procedure and by rigorously following sterile procedures have all contributed to a substantially reduced risk of contamination and infection. However, even when following the most rigorous procedures contamination may occur, particularly when the patient is being treated under emergency conditions. At best, a potentially contaminated catheter may have to be discarded prior to use when sterile procedures have not been followed.

A form of sterility sleeve used to maintain a portion of an indwelling catheter free from contamination for later use when it becomes necessary to re-position the catheter is disclosed in U.S. Pat. No. 4,327,723 to Paul L. Frankhouser. This sleeve is extended over a length of catheter immediately adjacent to the portion inserted into the vascular system of the patient, thereby physically isolating a reserve section of catheter from the atmosphere for use should it later become necessary to reposition the catheter.

U.S. Pat. No. 4,568,334 to Lawrence Lynn discloses a means for more comprehensive treatment of the contamination problem. In the Lynn patent, a combined storage, dispensing and preparation container is provided for an intravascular balloon catheter. The container includes a plurality of interconnected compartments in which different parts of the catheter are housed. Lynn's compartments include a test chamber for testing the integrity of the catheter balloon, an adjacent section in which a pleated sleeve is housed in what is termed a "trough compartment," a main compartment in which a substantial section of catheter may be stored and a connector compartment in which the proximal end of the catheter is located. The distal tip of the catheter is withdrawn from the test chamber once balloon integrity is tested, until the tip is located within the pleated sleeve by a pumping action of the sleeve. The pleated sleeve is then attached to a catheter introducer in place within the patient's blood vessel and the catheter is then advanced into the vessel by a reverse pumping action of the sleeve.

U.S. Pat. No. 4,622,033 to Taniguchi discloses a packaging construction for a urinary catheter comprising a lubricant reservoir and a tubular envelope or shield. A balloon-tipped urinary catheter is advanced into the lubricant reservoir prior to use. The lubricant reservoir has a frangible seal so that the reservoir can be removed once the catheter has been lubricated.

U.S. Pat. No. 4,637,404 to Gessman discloses a dispensing container for a cardiac pacing electrode in which a flexible sheath or sleeve comprising an accordion section 32 and another gathered or accordion section 34 is provided for advancing the electrode by grasping the wire through the sleeve.

OBJECTS AND ADVANTAGES OF THE INVENTION

The primary object of the present invention is the protection of a vascular catheter from contamination during testing and insertion of the catheter in a manner which maintains a substantial portion of the catheter not indwelling in the patient in physical isolation from the atmosphere for subsequent use as may be later required. A related object is the provision of a simple and effective means for testing, insertion and re-positioning of a vascular catheter in a way which always isolates the catheter from the hands of attending personnel as well as from airborne contaminants.

A still further object of the invention is the provision of simple and relatively inexpensive components for accomplishing the objectives just above mentioned.

A still further object of the invention is the provision of equipment for straightforward and trouble-free testing and insertion of a balloon-tipped vascular catheter which lends itself to unassisted use by a single attendant.

A still further object of the invention is the reduction in the number of catheters which must be discarded due to accidental contamination during testing and insertion of a vascular catheter.

Other objects and advantages of the invention will become apparent upon reference to the following detailed description of a preferred embodiment of the invention.

DETAILED DESCRIPTION OF THE DRAWINGS

In the drawings,

FIG. 1 is a view showing a catheter equipped with protective envelopes according to the invention, as the catheter is removed from its container and in condition ready for testing and subsequent use;

FIG. 2 is a fragmentary view showing, in perspective, portions of the structure of FIG. 1;

FIG. 3 is a sectional view of the portion of the structure illustrated in FIG. 2.

DETAILED DESCRIPTION OF THE INVENTION

Figure 4:
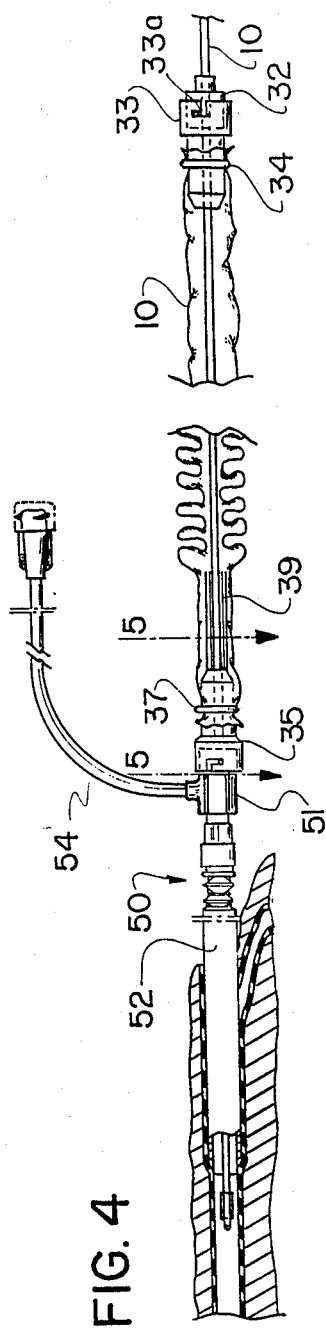
FIG. 4 is a view partly in section showing the catheter as the distal tip has just entered a blood vessel, such as the internal jugular vein.
Figure 5:
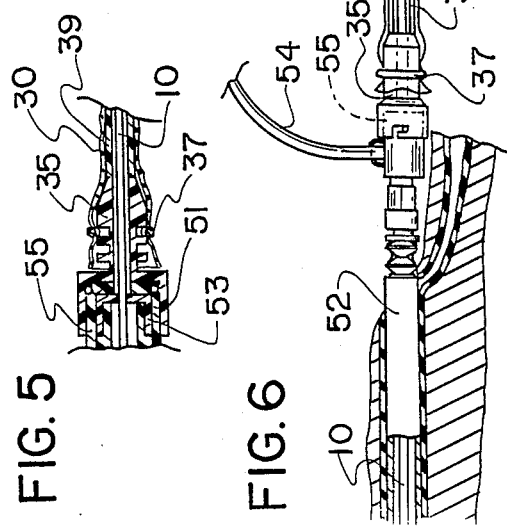
FIG. 5 is a sectional view through line 5—5 of FIG. 4.

Although the catheter illustrated in FIGS. 1-6 is a conventional four-lumen thermodilution catheter, other types of catheter may be advantageously provided with the sheath and test chamber construction of the present invention. Briefly stated, and by way of background, the catheter illustrated comprises an elongated flexible tubular body member 10 which typically has four passageways or lumens extending lengthwise therein. Body member 10 preferably has a pre-curved region adjacent the tip which is provided as an assistance to proper catheter placement as will be understood by those skilled in the art. Separately formed tubes or lumens 11–14 are respectively joined to the lumens of the catheter body member at the proximal end thereof within a molded fitting 15. Typically the tubes 11–14 are independently heat fused or adhesively joined to the lumens integrally formed within the body member so that four independent, non-communicating passages are formed. The proximal ends of the tubes 11, 12 and 14 are provided with Luer adapters or fittings 16–18 for connection to fluid devices. Fitting 18 is provided with a shut-off valve 19 for purposes to be explained hereinafter. The lumens joined to tubes 11 and 12 extend respectively to a port 20 at the catheter's distal tip and to a port 21 which is spaced approximately 30 centimeters from the distal tip. These lumens provide unimpeded flow passages for injecting fluids into the blood stream or for taking pressure measurements in a manner known in the art. The lumen joined to tube 13 houses leads for a thermistor 22 disposed within a port located within the pre-curved region on the inner side of the radius about 4 centimeters from the catheter's distal tip. The thermistor measures a change in temperature of a fluid ejected into the bloodstream through port 21 to provide a measurement of cardiac output as is well understood by those skilled in the art. For temperature measurement, the proximal end of tube 13 is equipped with an adapter 23 which houses an electrical connector for connecting the thermistor to suitable temperature-monitoring equipment. Finally, the lumen joined to tube 14 leads to the inflatable balloon 25 located just adjacent to the distal tip of the catheter. This lumen provides an uninterrupted flow passage for injecting an inflation media applied through adapter fitting 18 for inflation of the balloon 25. Valve 19 provides a means for closing this lumen once the balloon is properly inflated and allows for its deflation, as required. The catheter is also provided with suitable markings 26 at 10-centimeter intervals which give an indication to the user of the length of the catheter which has been inserted into the patient's blood vessel.

In carrying out the invention, there are two interconnected tubular envelopes provided for physically isolating all portions of the catheter that are liable to be inserted into the vascular system of the patient. The catheter is physically isolated from the atmosphere during testing of the balloon and flushing of fluid through the lumens by both envelopes. After testing, the distal end of the catheter is physically retracted into one of the envelopes and the other is discarded. During insertion, all portions not within the vascular system are protected by the remaining envelope. Still further, a substantial length of catheter is isolated for use during the time the catheter remains within the patient's vascular system. This reserve section is thus available in physical isolation within one of the envelopes without risk of contamination by the patient or attendants so that it may be used when repositioning the catheter as may be required. In its preferred form, the first envelope comprises an elongated flexible transparent tubular sheath 30 formed of a sheet-like impervious material which readily yields to finger pressure. The sheath surrounds the catheter and extends from a point adjacent the proximal end where it is secured to the catheter preferably via coupling means 31 comprising a hub 32 having a bore through which the catheter is passed. The hub is secured to the catheter by adhesive or other suitable means in a manner providing a substantially impervious seal. Hub 32 tightly interfits with a cylindrical coupling element 33. The parts are preferably locked in place by means of a slot 33a which receives a locking pin 32a projecting from hub 32. The proximal end of sleeve 30 fits over and is tightly secured to coupling element 33 by any suitable means such as elastic "O" ring 34 or by shrink fitting the sleeve directly onto the coupling element.

The distal end of sleeve 30 is secured to a second coupling means comprising coupling element 35 which has a throughbore 36 as shown in FIG. 3 which is sized to allow free passage for the catheter 10. Sealing means such as used in holding the proximal end of the sleeve on coupling element 33 affixed to the distal end of the sleeve to coupling 35. FIGS. 1–4 and 6 show an elastic "O" ring 37 for this purpose.

Figure 6:
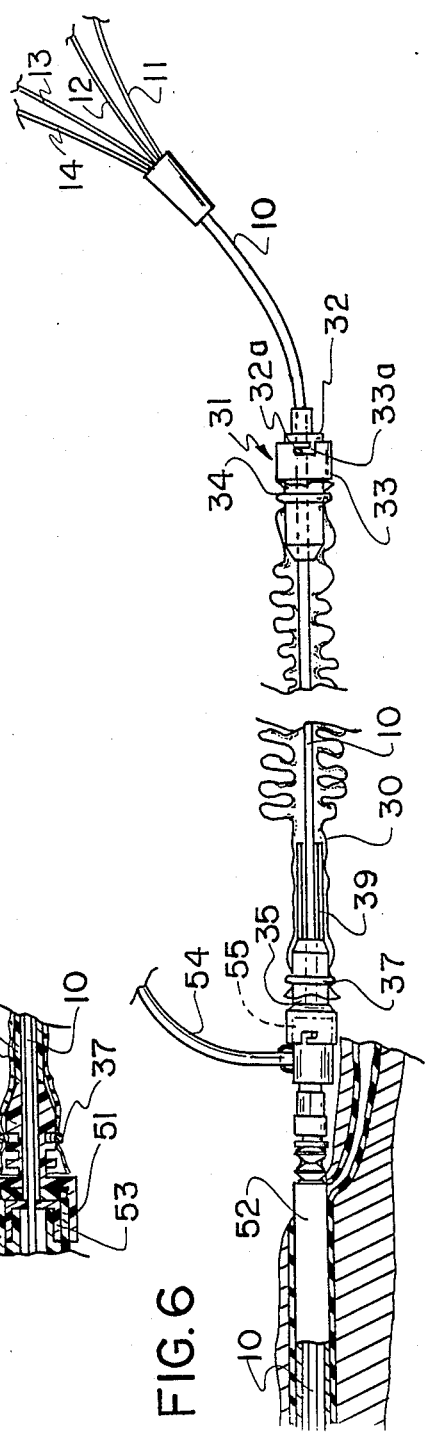
FIG. 6 is a view similar to FIG. 4, showing the catheter and the sleeve as the catheter is advanced further along into the blood vessel.

As can be seen in the drawings, particularly FIGS. 1, 4 and 6, the sleeve 30 is of large enough diameter relative to the catheter and is readily collapsible so that a substantial amount of relative axial movement can be achieved easily with the excess sleeve material being gathered or bunched up upon the catheter upon movement of the sleeve ends towards one another and being readily ungathered as the sleeve ends are separated. In overall length, the sleeve is capable of extension from a fixed point at 31 to the distal tip of the catheter.

Preferably a section of relatively flexible, somewhat resilient, plastic tubing 39 formed of polyurethane or the like extends rearwardly from the fitting 35 within sleeve 30. The tubing 39 is formed co-axially of the throughbore 36 and is dimensioned so that the catheter passes freely. The tubing 39 should have sufficient flexibility and resilience so that the application of a moderate amount of finger pressure exerted through sleeve 30 onto the outside walls of the tubing will compress the walls against the catheter, holding it in position against relative movement for reasons which will appear hereinafter.

The second envelope comprises a test chamber within which the distal portion of the catheter is to be positioned so that certain required tests, such as balloon inflation testing and catheter lumen patency, can be carried out and viewed in physical isolation from the environment immediately prior to use of the catheter. With reference to FIG. 1 which illustrates the position in which the catheter appears when the lid stock of the package in which it is stored in sterile condition is removed, the test chamber of the preferred embodiment of the invention comprises an elongated tube 40, preferably formed of transparent material so that the distal end of the catheter is exposed to view. When used with a catheter having a balloon at its distal tip, tube 40 has an enlarged end which may take the form of a separate cup or receptacle section 41 joined thereto, which is also preferably formed with a transparent wall section as shown in FIG. 1, which illustrates the position in which the catheter is ready to be tested. In this condition it is noted that the distal catheter tip with balloon 25 in the uninflated condition is preferably already within the cup 41 and the ejectate lumen 21 is within the tube 40. As is shown in FIGS. 2 and 3, the interior of the cup section 41 is large enough to provide ample clearance when the balloon is fully inflated. A vent is conveniently located in lid 42 as seen at 42a in FIG. 2, although a vent opening may be provided in other locations and in some instances may be unnecessary. Tube 40 may be a rigid tube with a pre-formed bend to accommodate the pre-formed bend common to pulmonary artery catheters, in its preferred form a flexible transparent tubing formed of polyurethane or the like is utilized. The flexible tubing is packaged with its end curved to the curvature of the distal end of the catheter having the pre-formed bend and it has been found that such tubing will take a nice set when sterilized after being positioned in the package with the required curvature. In FIG. 3, the curvature is not to scale and is somewhat exaggerated, it being shown for illustrative purposes only.

In order to releasibly interconnect the two envelopes, the proximal end of tube 40 carries a coupling hub member 43 which is of cylindrical shape so as to tightly fit into the cylindrical cavity 44 of coupling member 35 as may be best seen in FIGS. 2 and 3. Preferably a resilient sealing ring 45 fits within a recess 46 in the outer cylindrical wall of coupling member 43. Sealing ring 45 presses against the inner wall surface of the cylindrical cavity 44, providing a substantially air-impervious seal. The members are preferably locked together by releasible locking means which preferably comprises an L-shaped bayonet slot 47 on one member which receives pin 48.

As can best be seen in FIG. 1, the combined length of the envelope comprised of tube 40 and cup 41 is sufficient to extend proximally of catheter ejectate port 21 when the catheter is positioned with its distal tip within cup 41. As seen in FIGS. 2 and 3, tube 40 has a large enough internal diameter relative to catheter 10 to allow for free flow of liquid downwardly into cup 41 when the cup is held below the level of the ejectate port.

As indicated above, the catheter is packaged with the two envelopes interconnected by the coupling parts 35 and 43 so that a section of catheter (hereinafter sometimes called the "insertion zone"), comprising the entire length of the catheter running from the distal tip that is liable to be inserted into the patient's vascular system, is physically isolated from the ambient. When the lid stock is removed from the container tray (not shown) within which the catheter and other items needed for its use are housed, all portions, except for that portion proximal of the fitting 31, are thus in physical isolation. The user removes the assembly comprising the catheter housed within its protective envelopes from the tray and commences the test procedure, positioning the test chamber envelope below the level of the remainder of the catheter. By injecting saline solution through the fitting 16, one can visually observe the flow of solution which flows down tube 40 from ejectate port 21, thus simultaneously flushing the lumen 11 and verifying that it is unobstructed. During this phase of the test procedure, the tube 10 and the receptacle 41 are allowed to incline downwardly so that saline solution flowing out through port 21 freely flows towards receptacle 41. The user next injects saline solution through Luer fitting 17 and tubular lumen 12 thus flushing this lumen and filling the receptacle with saline solution. The balloon is then inflated by injecting a charge of inflation medium through Luer fitting 18. The balloon can be visually observed through the clear walls of cup 41. Symmetry of the balloon can be seen and leaks detected through the presence of bubbles flowing upwardly through the clear saline solution. If no leaks are detected and the balloon is seen to be appropriately symmetrical, the balloon is thereupon deflated. The distal end of the catheter is now ready to be extracted from the envelope comprising the test chamber.

To retract the catheter from the test chamber comprising tube 40 and cup 41, the front hub 35 is held by one hand and the rear hub by the other and the bunched material of sleeve 30 extended by physically separating the hubs. Since the sheath is as long as the catheter, the distal catheter tip is now within the hub 35. As the catheter is withdrawn from the test chamber, a resilient wiper 44a shown in FIG. 3 squeegees saline solution from the catheter back into the test chamber.

The test chamber is then removed by disconnecting coupling member 43 from coupling member 35 and discarded. The catheter is now ready for insertion into the vascular system of the patient.

Although the catheter may be inserted into a blood vessel by use of other techniques, it is preferably introduced using a standard sheath introducer 50 of known construction (FIGS. 4 and 6). As is known in the art, introducer 50 comprises a hollow valve body 51, and a thin walled sheath 52 which is adapted to be inserted into a blood vessel as schematically shown in FIGS. 4 and 6. The introducer assembly also includes a soft rubber hemostasis valve 53, located within hollow valve body 51 to inhibit back-bleeding. The valve is provided with a narrow slit, not shown, which is biased to close when catheter 10 is not in place and yields to form a seal around the catheter when the latter is introduced. Body 51 is further provided with a side port 54 which communicates with the interior of sheath 52 for fluid replacement and blood sampling if necessary prior to and during placement of the catheter.

The front connector element 35 is sized to interfit with a male connector 55 formed integrally with valve body 51. The connector parts are configured to provide a seal against air or airborne contaminants.

FIG. 4 illustrates the catheter with its distal tip advanced to a point just beyond the distal end of sheath 52. In order to advance the catheter, it is grasped through the sheath between the thumb and forefinger of one hand at a point five to ten centimeters behind hub 35 and gently pushed forwardly so that the distal tip passes through the introducer into the blood vessel. At the end of each forward stroke by the one hand the grip on the catheter is relaxed and the thumb and forefinger of the other hand apply pressure through tube 39 to hold the catheter in place while the gathered material of sheath 30 is moved away from the hub 35 in a reverse stroking motion. A series of forward and reverse strokes, while holding the catheter against movement on each reverse stroke, effect advancement of the catheter to the wedge position. If re-positioning becomes necessary, a reserve section of catheter extended from front hub 35 to rear hub 32 is always maintained in contamination-free condition.

The catheter may be partially withdrawn during re-positioning with the same series of forward and reverse strokes with the exception that the catheter is grasped with the thumb and forefinger of the stroking hand on the reverse stroke and held against movement by pressure exerted through tubing 39 by the thumb and forefinger of the other hand on the forward stroke. To effect complete withdrawal proximal hub 31 may be grasped and gently pulled backwardly until the catheter is fully retracted into sheath 30 or the distal hub 35 may be disconnected from the introducer and the catheter directly grasped and withdrawn.

Through use of the two envelopes, it can be seen that all portions of the catheter which may be introduced into the vascular system can be protected from external contamination from the time of sterilization until the catheter is withdrawn from the patient. During testing the balloon and all fluid flow ports on the body of the catheter are within the envelope comprising the test chamber and can be readily inspected and tested prior to catheter use. Saline solution flushed through ports 20 and 21 is confined to the test chamber. Following testing and immediately prior to use, all portions of the catheter are within the other envelope. In emergency conditions, the catheter can be tested and manipulated even without protective gloves should that be necessary.

I claim:

1. Equipment for shielding an elongated vascular catheter comprising a first impervious envelope for said catheter, said first envelope comprising a flexible, collapsible tubular sleeve, said sleeve being adapted to fit over the catheter in shielding relationship therewith and having a length relative to the length of said catheter to extend in shielding relationship therewith proximally from the distal tip of the catheter over all portions of the catheter subject to insertion into a vessel in the vascular system of a patient, said sleeve having a seal means at its proximal end for establishing a seal proximally of the portions of the catheter subject to insertion into the vessel, said sleeve being collapsible axially from the distal end thereof to allow for extension of the catheter beyond the distal end of the sleeve upon relative manual manipulation of the sleeve and of the catheter through the sleeve, a second impervious envelope for the distal end of the catheter, disconnectible means for connection of said second envelope to the distal end of the sleeve comprising said first envelope, said second envelope comprising a test chamber and a passage means extending from the said sleeve of said first envelope through said disconnectible means to said test chamber, said test chamber having a transparent end portion, said passage means allowing for positioning of the distal end of said catheter within the transparent end portion of the test chamber for visual inspection and testing when the sleeve is collapsed axially from said extended condition and for positioning of the distal end of the catheter within the first envelope when the sleeve is returned to said extended condition by relative manipulation of the sleeve and the catheter, said disconnectible means providing for removal of said second envelope when the sleeve is extended and for subsequent passage of the catheter from said first envelope into the vessel as the sleeve is collapsed from said extended condition.

2. Equipment according to claim 1 wherein said catheter is a multi-lumen flow directed catheter with an inflatable balloon adjacent the distal tip, and wherein said transparent end portion of the test chamber is sized to allow for clearance for the balloon when the balloon is within the test chamber and in the inflated state.

3. Equipment according to claim 2 wherein said catheter has an ejectate port spaced proximally of the balloon and wherein the test chamber is sized to simultaneously receive the balloon and the ejectate port.

4. Equipment according to claim 3 wherein said catheter is provided with a second ejectate port at the distal tip and wherein the transparent end portion of the test chamber comprises a receptacle of substantially rigid plastic material for accumulating liquid ejected through said ports.

5. Equipment according to claim 4 wherein said test chamber further comprises a tubular member formed of a relatively flexible, transparent material, said tubular member being connected to said passage means and said receptacle, said tubular member allowing clearance for said catheter and for the flow of liquid from the ejectate port which is spaced proximally of said balloon.

6. Equipment according to claim 5 further including a resilient wiper within said passage means, said wiper being in contact with said catheter at a point in said passageway spaced proximally of said balloon and said ejectate ports.

7. Equipment according to claim 1, said disconnectible means comprising means for freely suspending the second envelope from the distal end of the sleeve comprising said first envelope.

8. Means for physically isolating a balloon-tipped vascular catheter from contaminants, said catheter having a distal end with a distal tip and a port at the distal tip, an inflatable balloon adjacent said tip and independent lumens within the catheter connected to and extending lengthwise respectively from the port at the distal tip and from said inflatable balloon to the proximal end of the catheter, said catheter further having an insertion zone extending from said distal tip lengthwise thereof to a point adjacent the proximal end, said zone being adapted to be inserted into a blood vessel of a patient, a flexible sleeve having a length at least as long as the insertion zone, said sleeve being collapsible to cover that portion of the zone not inserted within the patient's blood vessel, the proximal end of the sleeve being fixedly secured to the catheter at the proximal end of the insertion zone in sealing relationship therewith, a hub slidably mounted on said catheter, means sealing the distal end of the sleeve to the hub, said sleeve allowing for manual manipulation of the catheter by pressure contact through the sleeve with the users' fingers for axial movement of the catheter, an enclosed test chamber for testing the integrity of the balloon when the balloon is in an inflated state and having a transparent wall portion for viewing of the balloon, a passageway connecting the test chamber with the sleeve, said passageway providing for placement of the distal tip of the catheter from a position adjacent the hub to a position within the test chamber, for retraction of the catheter to a position within the sleeve when the sleeve is extended, and disconnectible coupling means for disconnecting the hub from the test chamber when the distal end of the catheter is moved to a position within said sleeve, said catheter being axially moveable into a blood vessel by manipulation through said sleeve when the hub is disconnected from said test chamber.

9. Apparatus according to claim 8 wherein said test chamber is adapted to accumulate liquid discharged through said distal catheter port.

10. Apparatus according to claim 9 wherein said catheter has an ejectate port spaced proximally of the balloon and wherein said test chamber includes a tubular conduit through which said catheter extends, said conduit extending in a lengthwise direction proximally of said ejectate port when the distal catheter tip is within the test chamber whereby liquid discharged through said ejectate port accumulates in said test chamber.

11. Apparatus according to claim 9 wherein said tubular conduit is formed of a transparent material.

12. Apparatus according to claim 11 wherein said tubular conduit is formed of a flexible material.

13. Apparatus according to claim 9 further including a vent for said test chamber.

14. In combination with a vascular catheter having an elongated body portion and a distal tip and at least one lumen extending lengthwise of the catheter and exiting in the region of the distal tip, said catheter having an insertion zone for insertion into a blood vessel of a patient, said zone extending from the distal tip lengthwise of the body portion, a flexible and axially collapsible and extendable sleeve having a length at least equal to the length of the insertion zone, said sleeve being adapted to fit over the catheter so as to shield the catheter from contamination, means fixedly securing the proximal end of the sleeve to the catheter body portion at the proximal end of the insertion zone and in sealing relationship with said body portion, a hub slidably mounted on said catheter, means fixing the distal end of the sleeve to the hub in sealing relationship therewith, a test envelope adapted to receive the distal end of said catheter including said distal tip and a portion of said insertion zone, said test envelope having a transparent wall portion for viewing of the distal tip region of the catheter, disconnectible coupling means for connecting said hub to said test envelope, a passageway extending from the sleeve interior through said coupling means into the test envelope, said passageway being sized to pass the distal end of the catheter from the sleeve into the test envelope, said catheter being movable by manual manipulation through the sleeve from the test envelope into the sleeve and for subsequent advancement of the catheter from the sleeve into a blood vessel of the patient when the test envelope is disconnected.

15. Equipment according to claim 14 wherein the sleeve length relative to the length of the insertion zone is such that the distal tip of the catheter is withdrawn out of the test envelope into shielding relation with said sleeve when the sleeve is fully extended.

16. Equipment according to claim 15 wherein said test envelope comprises a flexible transparent tubing portion extending from said coupling means and a rigid walled receptacle at the distal end of said tubing portion in communication therewith, said rigid walled receptacle incorporating said transparent wall portion for viewing of the distal tip region of the catheter and the passageway extending through the tubing portion into the receptacle.

17. Equipment according to claim 16 wherein said test envelope is connected to said sleeve solely through said coupling means whereby the test envelope may be separated from the catheter and the sleeve and discarded when the catheter is advanced from the sleeve into a blood vessel.

* * * * *